US012677921B2

(12) United States Patent
Milic et al.

(10) Patent No.: US 12,677,921 B2
(45) Date of Patent: Jul. 14, 2026

(54) DEVICE FOR THE OXIDATION DYEING OF KERATIN FIBRES

(71) Applicant: L'Oreal, Paris (FR)

(72) Inventors: Mladen Milic, St. Ouen (FR); David Seneca, St. Ouen (FR)

(73) Assignee: L'OREAL, Paris (FR)

( * ) Notice: Subject to any disclaimer, the term of this patent is extended or adjusted under 35 U.S.C. 154(b) by 322 days.

(21) Appl. No.: 18/560,154

(22) PCT Filed: May 12, 2022

(86) PCT No.: PCT/EP2022/062975
§ 371 (c)(1),
(2) Date: Nov. 10, 2023

(87) PCT Pub. No.: WO2022/238545
PCT Pub. Date: Nov. 17, 2022

(65) Prior Publication Data
US 2024/0225232 A1      Jul. 11, 2024

(30) Foreign Application Priority Data

May 12, 2021    (FR) ...................................... 2105046

(51) Int. Cl.
*A61Q 5/10*          (2006.01)
*A45D 19/00*        (2006.01)
(Continued)

(52) U.S. Cl.
CPC ............ *A45D 19/0066* (2021.01); *A61K 8/22* (2013.01); *A61K 8/345* (2013.01); *A61Q 5/10* (2013.01);
(Continued)

(58) Field of Classification Search
CPC .... A45D 19/0066; A45D 34/042; A61K 8/22; A61K 8/345; A61K 2800/548;
(Continued)

(56) References Cited

U.S. PATENT DOCUMENTS

| | | | |
|---|---|---|---|
| 7,070,769 B2 * | 7/2006 | Ascione | A61K 8/8152 |
| | | | 252/186.25 |
| 2004/0205902 A1 * | 10/2004 | Cottard | A61Q 5/10 |
| | | | 8/405 |

(Continued)

FOREIGN PATENT DOCUMENTS

| | | | | |
|---|---|---|---|---|
| FR | 3060372 | 6/2018 | | |
| WO | WO 2020002154 A1 * | 1/2020 | | A61Q 5/065 |

(Continued)

OTHER PUBLICATIONS

International Search Report and Written Opinion for PCT/EP2022/062975 (International Filing Date: May 12, 2022), mailed Jul. 12, 2022, (17 pages).

*Primary Examiner* — Eisa B Elhilo
(74) *Attorney, Agent, or Firm* — CHRISTENSEN O'CONNOR JOHNSON KINDNESS PLLC

(57) ABSTRACT

The present invention relates to a device (1) for dyeing keratin fibres, comprising at least two compartments (2) and (3), the first compartment (2) comprising a first composition (A) comprising oxidation dyes and the second compartment (3) comprising a second composition (B) comprising chemical oxidizing agents. Said device allows easy mixing of the compositions contained in said compartments at the time of use.

19 Claims, 1 Drawing Sheet

(51) Int. Cl.
  *A61K 8/22*     (2006.01)
  *A61K 8/34*     (2006.01)

(52) U.S. Cl.
  CPC .. *A61K 2800/548* (2013.01); *A61K 2800/882*
               (2013.01)

(58) Field of Classification Search
  CPC .. A61K 2800/882; A61K 8/342; A61K 8/415;
         A61K 8/8152; A61Q 5/10
  USPC .......................................................... 8/405
  See application file for complete search history.

(56)       References Cited

U.S. PATENT DOCUMENTS

| | | | |
|---|---|---|---|
| 2005/0000037 A1* | 1/2005 | Audousset | A61K 8/87 |
| | | | 8/405 |
| 2005/0000039 A1* | 1/2005 | Audousset | A61K 8/731 |
| | | | 8/405 |
| 2007/0209124 A1 | 9/2007 | Bureiko et al. | |
| 2015/0053228 A1* | 2/2015 | Bonauer | A61K 8/55 |
| | | | 132/208 |

FOREIGN PATENT DOCUMENTS

| | | |
|---|---|---|
| WO | WO 2020/093283 | 5/2020 |
| WO | WO 2020/258220 | 12/2020 |

* cited by examiner

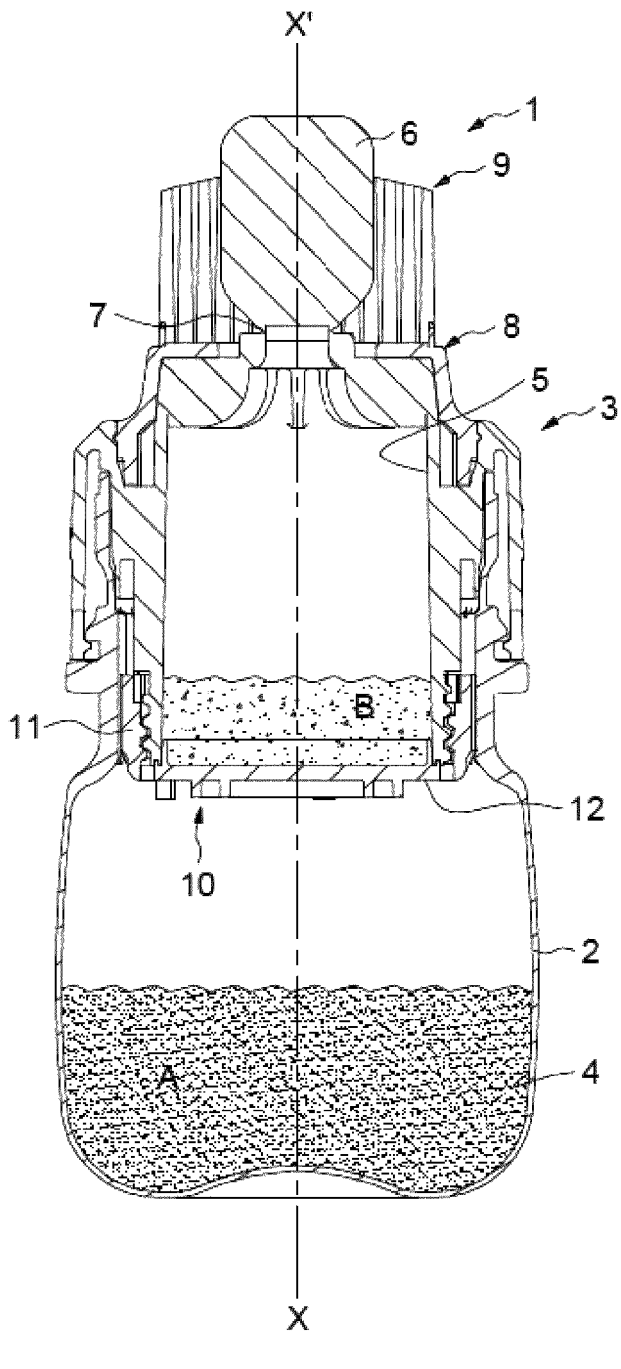

DEVICE FOR THE OXIDATION DYEING OF KERATIN FIBRES

The present application is a National Stage Application of PCT/EP2022/062975, filed May 12, 2022, which claims the benefit of FR2105046, filed May 12, 2021, the disclosures of which are incorporated herein in their entirety.

The present invention relates to a device for dyeing keratin fibres, comprising at least two compartments, the first compartment comprising a composition comprising oxidation dyes and the second compartment comprising a composition comprising chemical oxidizing agents. Said device allows easy mixing of the compositions contained in said compartments at the time of use.

The present invention also relates to a process for treating keratin fibres, in particular human keratin fibres such as the hair.

The invention also relates to the use of said device for dyeing keratin fibres, in particular human keratin fibres such as the hair.

Conventional oxidation dyeing processes generally consist in applying to keratin fibres a dye composition comprising oxidation bases and couplers with an oxidizing composition comprising hydrogen peroxide ($H_2O_2$ or aqueous hydrogen peroxide solution), in leaving it to stand on the fibres, and then in rinsing said fibres. These dyeing processes are appreciated by users since the colourings resulting therefrom are generally permanent, strong and resistant to external agents, notably to light, bad weather, washing, perspiration and rubbing.

These dyeing processes require the mixing, at the time of use, of the dye composition and of the oxidizing composition. This operation has the drawback of staining the hands of the user or of the hairstylist.

Moreover, the resulting composition is not easy to apply and may also give rise to undesirable stains on the user's scalp, contour of the face and/or clothing, which may be due to application errors and/or to problems of running of the compositions.

Furthermore, it may prove difficult to perform precise and uniform application of the composition on the keratin fibres, resulting in unsatisfactory colouring.

In addition, for optimum colouring, the dye composition and oxidizing composition must be mixed in a precise amount. This is no easy matter with the kits (or devices) that are available on the market.

In particular, restitution of the dyeing mixture at the outlet of the devices currently used may prove to be insufficient, which leads to unsatisfactory colourings.

There is thus a real need to overcome the drawbacks mentioned previously in the context of oxidation dyeing, notably the difficulties associated with the mixing of the dye composition and oxidizing composition and the application of the resulting composition.

This aim is achieved by the present invention, the subject of which is notably a device comprising at least two compartments:

i) a first compartment comprising a first composition A comprising:
   one or more oxidation dyes, and
   one or more acrylic anionic associative polymers;
ii) a second compartment comprising a second composition B comprising:
   one or more chemical oxidizing agents,
   one or more fatty alcohols and/or one or more nonionic surfactants, and
   optionally one or more polyols, said device being configured to allow said compartments to be placed in communication so as to enable the mixing of said compositions in one of said compartments.

FIG. 1 shows one embodiment of the device according to the invention.

The device of the invention allows easy and precise mixing of the dye composition and oxidizing composition, without any risk of staining the user's hands.

The device also allows easy handling of the resulting composition by the user for the purpose of applying it to keratin fibres.

The device may optionally allow the application of the resulting composition directly onto the keratin fibres.

The resulting composition affords strong, chromatic, sparingly selective colourings that are resistant to external attacking factors notably such as light, perspiration and shampoo washing.

The present invention also relates to a process for treating keratin fibres, in particular human keratin fibres such as the hair, using the device as described above.

A subject of the invention is also the use of said device for dyeing keratin fibres, in particular human keratin fibres such as the hair.

Other subjects, characteristics, aspects and advantages of the invention will emerge even more clearly on reading the description, the FIGURE and the examples that follow.

The limits of a range of values are included in that range, notably in the expressions "between . . . and . . . " and "ranging from . . . to . . . ". The expression "at least one" is equivalent to the expression "one or more" and may be replaced therewith.

Device

The device of the invention comprises at least two compartments, each comprising a composition A or B as defined above. The device enables two compositions to be contained separately, the two compartments not being in fluid communication in a first position.

Said device is configured to allow said compartments to be placed in communication so as to enable the mixing of said compositions in one of said compartments before use.

In other words, the device is configured to enable said compartments to be placed in fluid communication.

The compartments may be placed in communication by various means.

In one embodiment, the compartments of the device are assembled one above the other.

In one embodiment, said compartments can move relative to each other on a vertical axis so as to release a passage between the at least two compartments allowing two compartments to be placed in communication, and mixing of the two compositions.

As a variant, said compartments can rotate relative to each other on a vertical axis so as to release a passage between the two compartments allowing two compartments to be placed in communication, and mixing of the two compositions.

In one embodiment, the at least two compartments of the device are separated by at least one temporary shut-off member.

The temporary shut-off member is intended to be at least partly detached.

Preferably, the temporary shut-off member is configured to close an open end of one of said compartments before use.

Preferably, the temporary shut-off member comprises a cylindrical skirt surrounding said open end and a stopper connected to said cylindrical skirt.

Preferably, said compartments are capable of rotating relative to each other without moving axially.

Rotation of the compartments relative to each other by the user allows the rupture of the shut-off member and thus their placing in communication, thereby enabling the mixing of the compositions contained in these compartments.

In other words, during use, the shut-off member becomes at least partly detached, which enables said compartments to be placed in fluid communication.

The device may also comprise at least one dispensing orifice for dispensing the ready-to-use composition obtained after mixing. The dispensing orifice may be closed by means of a closing member.

The device may also comprise an applicator for facilitating the application of the ready-to-use composition. The applicator may be, for example, a comb, a fine brush or a coarse brush. The applicator may be placed in fluid communication with the interior of the compartment in which the mixing is performed so as to allow the ready-to-use composition to reach the applicator in order to be applied to the hair.

Advantageously, the ready-to-use composition is applied directly using the device via the dispensing orifice, optionally comprising an applicator. In other words, the ready-to-use composition is not taken up in the device. Thus, the device of the invention facilitates the application of the composition and affords an improved rate of restitution of said ready-to-use composition.

In addition, the application and dispensing of the ready-to-use composition do not require a pump or a propellant. The ready-to-use composition flows by gravity via the dispensing orifice. A pressure may optionally be applied to the container to facilitate the flow and dispensing of the ready-to-use composition.

Such devices are described, for example, in patent applications WO 2020/093281, WO 2020/093282 and WO 2020/093283.

FIG. 1 shows one embodiment of the device of the invention.

FIG. 1 is a view in longitudinal cross section of a device 1 according to the invention comprising two compartments 2, 3. The axis X-X' represents a vertical axis. The first compartment 2 defines an internal cavity 4 comprising a first composition A as described previously. The second compartment 3 defines an internal cavity 5 comprising a second composition B as described previously.

The two compartments 2, 3 are separated by a temporary shut-off member 10 for closing an open end between the two compartments. This temporary shut-off member 10 comprises a cylindrical skirt 11 surrounding said open end and a stopper 12 connected to said cylindrical skirt 11.

The second compartment 3 comprises a dispensing orifice 7 closed by a closing member 6.

The second compartment 3 also comprises an applicator 8 surrounding the dispensing orifice 7. The applicator 8 comprises a plurality of teeth 9 regularly distributed all around the dispensing orifice 7, thus forming an applicator in comb form.

Preferably, the device 1 according to the invention comprises:
  i) a first compartment 2 comprising a first composition A comprising:
    one or more oxidation dyes, and
    one or more acrylic anionic associative polymers;
  ii) a second compartment 3 comprising a second composition B comprising:
    one or more chemical oxidizing agents, one or more fatty alcohols and/or one or more nonionic surfactants, and
    optionally one or more polyols,
  said device being configured to allow said compartments to be placed in communication so as to enable the mixing of said compositions in one of said compartments 2, 3, said compartments being separated by at least one temporary shut-off member 10 intended to be at least partly detached.

Preferably, the second compartment 3 comprises a composition containing one or more chemical oxidizing agents, one or more fatty alcohols and one or more nonionic surfactants, and optionally one or more polyols.

The Oxidation Dyes

The first composition A included in the first compartment 2 of the device 1 of the invention comprises one or more oxidation dyes.

The oxidation dyes may be chosen from one or more oxidation bases, optionally in combination with one or more couplers.

Preferably, the oxidation dye(s) comprise one or more oxidation bases.

The oxidation bases may be chosen from para-phenylenediamines, bis(phenyl)alkylenediamines, para-aminophenols, ortho-aminophenols and heterocyclic bases, the addition salts thereof, the solvates thereof, and solvates of the salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(p-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-γ-hydroxypropyl-para-phenylenediamine; 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid, the solvates thereof, and solvates of the salts thereof.

Among the para-phenylenediamines mentioned above, para-phenylenediamine, para-tolylenediamine, 2-isopropyl-para-phenylenediamine, 2-β-hydroxyethyl-para-phenylenediamine, 2-methoxymethyl-para-phenylenediamine, 2-γ-hydroxypropyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-paraphenylenediamine, the addition salts thereof with an acid, the solvates thereof, and solvates of the salts thereof are particularly preferred.

Among the bis(phenyl)alkylenediamines, examples that may be mentioned include N,N'-bis(β-hydroxyethyl)-N,N'-bis(4'-aminophenyl)-1,3-diaminopropane, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, the addition salts thereof, the solvates thereof, and solvates of the salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, the addition salts thereof with an acid, the solvates thereof, and solvates of the salts thereof.

Among the ortho-aminophenols, examples that may be mentioned include 2-aminophenol, 2-amino-5-methylphenol, 2-amino-6-methylphenol and 5-acetamido-2-aminophenol, the addition salts thereof, solvates thereof and solvates of the salts thereof.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, 3,4-diaminopyridine, the addition salts thereof, the solvates thereof, and solvates of the salts thereof.

Other pyridine oxidation bases that are useful in the present invention are the 3-aminopyrazolo[1,5-a]pyridine oxidation bases or their addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and 2-(3-amino-pyrazolo[1,5-a]pyridin-2-yl)oxyethanol, the addition salts thereof, the solvates thereof, and solvates of the salts thereof.

Among the pyrimidine derivatives, mention may be made of the compounds described, for example, in patents DE 2359399, JP 88-169571, JP 05-63124 and EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, the addition salts thereof, the solvates thereof, and solvates of the salts thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt thereof, the solvates thereof, and solvates of the salts thereof.

Pyrazole derivatives that may also be mentioned include diamino-N,N-dihydropyrazolopyrazolones and notably those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof, the solvates thereof, and solvates of the salts thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or 2-(3-aminopyrazolo[1,5-a]pyridin-2-yl)oxyethanol and/or a salt thereof, the solvates thereof, and solvates of the salts thereof.

The oxidation dye(s) may also comprise one or more couplers, which may be chosen from the couplers conventionally used for the dyeing of keratin fibres.

Preferably, the couplers are chosen from meta-phenylenediamines, meta-aminophenols, meta-diphenols, naphthalene-based couplers and heterocyclic couplers, and also the addition salts thereof, the solvates thereof, and/or solvates of the salts thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 1-methyl-2-hydroxy-4-β-hydroxyethylaminobenzene, 4-amino-2-hydroxytoluene, 5-amino-6-chloro-2-methylphenol, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 5-methoxy-6-hydroxyindole, 2-amino-3-hydroxypyridine, 6-hydroxybenzomorpholine, 2-amino-4-hydroxyethylaminoanisole, 3-amino-6-methoxy-2-methylaminopyridine, 3,5-diamino-2,6-dimethoxypyridine, 1-N-(β-hydroxyethyl)amino-3,4-methylenedioxybenzene, 2,6-bis(p-hydroxyethylamino) toluene, 6-hydroxyindoline, 2,6-dihydroxy-4-methylpyridine, 2-chloro-3,5-diaminopyridine, 2-chloro-3,5-diamino-6-methoxypyridine, 2-chloro-3,5-diamino-6-methylpyridine, 1-H-3-methylpyrazol-5-one, 1-phenyl-3-methylpyrazol-5-one, 4-(3,5-diaminopyridin-2-yl)-1-(2-hydroxyethyl)-1-methylpiperazin-1-ium chloride, 2,6-dimethylpyrazolo[1,5-b]-1,2,4-triazole, 2,4,6-trimethoxyaniline hydrochloride, 2,6-dimethyl[3,2-c]-1,2,4-triazole, 6-methylpyrazolo[1,5-a]benzimidazole and 2,6-diaminopyrazine, the addition salts thereof, the solvates thereof, and/or solvates of the salts thereof, and mixtures thereof.

Preferably, the coupler(s) used in the invention are chosen from 1,3-dihydroxybenzene, 1,3-dihydroxy-2-methylbenzene, 4-chloro-1,3-dihydroxybenzene, 1-hydroxy-3-aminobenzene, 1-methyl-2-hydroxy-4-β-hydroxyethylaminobenzene, 4-amino-2-hydroxytoluene, 5-amino-6-chloro-2-methylphenol, 2,4-diamino-1-(β-hydroxyethyloxy)benzene, α-naphthol, 6-hydroxyindole, 2-amino-3-hydroxypyridine, 6-hydroxybenzomorpholine, 3-amino-6-methoxy-2-methylaminopyridine, 2-amino-4-hydroxyethylaminoanisole, hydroxyethyl-3,4-methylenedioxyaniline and 2-amino-5-ethylphenol, the addition salts thereof, the solvates thereof, and/or solvates of the salts thereof, and mixtures thereof.

Even more preferentially, the coupler(s) used in the invention are chosen from 3-amino-6-methoxy-2-methylaminopyridine, 6-hydroxybenzomorpholine, 2,4-diamino-1-(β-hydroxyethyloxy)benzene, 2-amino-3-hydroxypyridine, 5-amino-6-chloro-2-methylphenol, 1-methyl-2-hydroxy-4-β-hydroxyethylaminobenzene, 2-amino-4-hydroxyethylaminoanisole, hydroxyethyl-3,4-methylenedioxyaniline, 2-amino-5-ethylphenol and 1-hydroxy-3-aminobenzene, the addition salts thereof, the solvates thereof, and/or solvates of the salts thereof, and mixtures thereof.

In general, the addition salts of the couplers that may be used within the context of the invention are notably chosen from the addition salts with an acid such as the hydrochlorides, hydrobromides, sulfates, citrates, succinates, tartrates, lactates, tosylates, benzenesulfonates, phosphates and acetates.

Preferably, the oxidation dyes chosen from bases are chosen from para-phenylenediamine, para-tolylenediamine, 2-β-hydroxyethyl-para-phenylenediamine, 2-methoxymethyl-para-phenylenediamine, 2-γ-hydroxypropyl-para-phenylenediamine, N,N-bis(β-hydroxyethyl)-para-phenylenediamine, N,N'-bis(β-hydroxyethyl)-N,N'-bis(4'-aminophenyl)-1,3-diaminopropanol, para-aminophenol, 4-amino-3-methylphenol, para-aminophenol, 4-amino-3-methylphenol, 2,3-diamino-6,7-dihydro-1H,5H-pyrazolo[1,2-a]pyrazol-1-one, 2-(3-aminopyrazolo[1,5-a]pyridin-2-yl) oxyethanol, the addition salts thereof, the solvates thereof, and/or solvates of the salts thereof.

Preferably, the oxidation dyes chosen from couplers are chosen from 6-hydroxybenzomorpholine, 2,4-diamino-1-(β-hydroxyethyloxy)benzene, 2-amino-3-hydroxypyridine, 5-amino-6-chloro-2-methylphenol, 1-methyl-2-hydroxy-4-β-hydroxyethylaminobenzene, 2-amino-4-hydroxyethylaminoanisole, hydroxyethyl-3,4-methylenedioxyaniline, 2-amino-5-ethylphenol, 1-hydroxy-3-aminobenzene, the addition salts thereof, the solvates thereof, and/or solvates of the salts thereof, and mixtures thereof.

Advantageously, the oxidation dyes chosen from oxidation bases are present in a total content ranging from 0.0001% to 10% by weight, preferably from 0.005% to 7% by weight and more preferentially from 0.1% to 4% by weight, relative to the total weight of the first composition A.

Advantageously, the oxidation dyes chosen from couplers are present in a total content ranging from 0.0001% to 10% by weight, preferably from 0.005% to 7% by weight and more preferentially from 0.1% to 4% by weight, relative to the total weight of the first composition A.

Advantageously, the oxidation dyes are present in a total content ranging from 0.0001% to 10% by weight, preferably from 0.005% to 7% by weight, and more preferentially from 0.1% to 5% by weight, relative to the total weight of the composition comprising them.

The Acrylic Anionic Associative Polymers

The first composition A included in the first compartment 2 of the device 1 of the invention comprises one or more acrylic anionic associative polymers.

For the purposes of the present invention, the term "acrylic polymer" means a polymer comprising at least one unit derived from an α,β-monoethylenically unsaturated carboxylic acid monomer, derivatives thereof and/or salts thereof, preferably chosen from acrylic acid, methacrylic acid, derivatives thereof and/or salts thereof.

It is recalled that "associative polymers" are polymers that are capable, in an aqueous medium, of reversibly associating with each other or with other molecules.

Their chemical structure more particularly comprises at least one hydrophilic zone and at least one hydrophobic zone.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the associative polymers of acrylic anionic type that may be mentioned are:
(a) those including at least one hydrophilic unit and at least one fatty-chain allyl ether unit, more particularly those whose hydrophilic unit is formed by an ethylenic unsaturated anionic monomer, more particularly a vinylcarboxylic acid and most particularly an acrylic acid or a methacrylic acid or mixtures thereof.

Among these acrylic anionic associative polymers, the ones that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl (meth)acrylate, divinylbenzene, (poly) ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), notably those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);

(b) those including i) at least one hydrophilic unit of unsaturated olefinic carboxylic acid type, and ii) at least one hydrophobic unit of the ($C_{10}$-$C_{30}$) alkyl ester of an unsaturated carboxylic acid type.

($C_{10}$-$C_{30}$) Alkyl esters of unsaturated carboxylic acids that are useful in the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to patents U.S. Pat. Nos. 3,915,921 and 4,509,949.

Among the acrylic anionic associative polymers of this type that will be used more particularly are those constituted of from 95% to 60% by weight of acrylic acid (hydrophilic unit), 4% to 40% by weight of $C_{10}$-$C_{30}$ alkyl acrylate (hydrophobic unit) and 0 to 6% by weight of crosslinking polymerizable monomer, or alternatively those constituted of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described previously.

Among said polymers above, the ones most particularly preferred according to the present invention are the products sold by the company Goodrich under the trade names Pemulen TR1®, Pemulen TR2®, Carbopol 1382®, and even more preferentially Pemulen TR1®, and the product sold by the company SEPPIC under the name Coatex SX®.

Mention will also be made of the compounds sold by Lubrizol under the trade names Carbopol Ultrez 20 and Carbopol Ultrez 21 having the INCI name Acrylates/C10-C30 alkyl acrylate crosspolymer.

Mention may also be made of the acrylic acid/lauryl methacrylate/vinylpyrrolidone terpolymer sold under the name Acrylidone LM by ISP;

(c) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies.

(d) acrylic terpolymers comprising:
i) about 20% to 70% by weight of an α,β-monoethylenically unsaturated carboxylic acid [A],
ii) about 20% to 80% by weight of an α,β-monoethylenically unsaturated non-surfactant monomer other than [A], iii) about 0.5% to 60% by weight of a nonionic monourethane which is the product of reaction of a monohydric surfactant with a monoethylenically unsaturated monoisocyanate, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion;

(e) copolymers including among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

An example of a compound of this type that may be mentioned is Aculyn 22' sold by the company Röhm & Haas, which is a methacrylic acid/ethyl acrylate/oxyalkylenated stearyl methacrylate terpolymer; and also Aculyn 88, also sold by the company Rohm & Haas. Mention may also be made of Synthalen W2000L sold by the company 3V, having the INCI name Acrylates/Palmeth-25 acrylate copolymer, and Novethix-L-10 sold by the company Lubrizol, having the INCI name Acrylates/Beheneth-25 methacrylate copolymer;

(f) amphiphilic polymers including at least one ethylenically unsaturated monomer bearing a sulfonic group, in free or partially or totally neutralized form and comprising at least one hydrophobic part. These polymers may be crosslinked or non-crosslinked. They are preferably crosslinked.

The ethylenically unsaturated monomers bearing a sulfonic group are notably chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof.

(Meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2, 6-dimethyl-3-heptanesulfonic acid, and also partially or totally neutralized forms thereof, will more preferentially be used.

2-Acrylamido-2-methylpropanesulfonic acid (AMPS), and also partially or totally neutralized forms thereof, will more particularly be used.

The polymers of this family may be chosen notably from random amphiphilic AMPS polymers modified by reaction with a $C_6$-$C_{22}$ n-monoalkylamine or di-n-alkylamine, and such as those described in patent application WO 00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of this family are chosen from amphiphilic copolymers of AMPS and of at least one ethylenically unsaturated hydrophobic monomer.

These same copolymers may also contain one or more ethylenically unsaturated monomers not including a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described notably in patent application EP-A 750 899, patent U.S. Pat. No. 5,089,578 and in the following publications from Yotaro Morishima:
Self-assembling amphiphilic polyelectrolytes and their nanostructures, *Chinese Journal of Polymer Science*, Vol. 18, No. 40, (2000), 323-336;
Micelle formation of random copolymers of sodium 2-(acrylamido)-2-methylpropanesulfonate and a nonionic surfactant macromonomer in water as studied by fluorescence and dynamic light scattering, *Macromolecules*, Vol. 33, No. 10 (2000), 3694-3704;
Solution properties of micelle networks formed by nonionic moieties covalently bound to a polyelectrolyte: salt effects on rheological behavior, *Langmuir*, Vol. 16, No. 12, (2000), 5324-5332;
Stimuli responsive amphiphilic copolymers of sodium 2-(acrylamido)-2-methylpropanesulfonate and associative macromonomers, *Polym. Preprint, Div. Polym. Chem.* 40(2), (1999), 220-221.

Among these polymers, mention may be made of:
crosslinked or non-crosslinked, neutralized or non-neutralized copolymers, including from 15% to 60% by weight of AMPS units and from 40% to 85% by weight of $(C_8-C_{16})$alkyl(meth)acrylamide or $(C_8-C_{16})$alkyl (meth)acrylate units relative to the polymer, such as those described in patent application EP-A750 899;
terpolymers including from 10 mol % to 90 mol % of acrylamide units, from 0.1 mol % to 10 mol % of AMPS units and from 5 mol % to 80 mol % of n-$(C_6-C_{18})$alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Preferably, the acrylic anionic associative polymer(s) are chosen from copolymers including, among their monomers, an α,β-monoethylenically unsaturated carboxylic acid and an ester of an α,β-monoethylenically unsaturated carboxylic acid and of an oxyalkylenated fatty alcohol.

Advantageously, the acrylic anionic associative polymer (s) are present in a total content ranging from 0.01% to 5% by weight, preferably from 0.05% to 4% by weight, more preferentially from 0.1% to 3% by weight, and better still from 0.2% to 2% by weight, relative to the total weight of the composition comprising them.

Chemical Oxidizing Agents

The second composition B included in the second compartment 3 of the device 1 of the invention comprises one or more chemical oxidizing agents.

The term "chemical oxidizing agent" means chemical oxidizing agents other than atmospheric oxygen.

Preferably, the chemical oxidizing agent(s) are chosen from hydrogen peroxide, urea peroxide, alkali metal bromates, persalts such as perborates and persulfates, in particular sodium persulfate, potassium persulfate and ammonium persulfate, peracids and oxidase enzymes (with the optional cofactors thereof) such as peroxidases, 2-electron oxidoreductases such as uricases and 4-electron oxygenases such as laccases, and mixtures thereof; preferentially, the chemical oxidizing agent(s) are chosen from hydrogen peroxide, persalts, and mixtures thereof; better still, the chemical oxidizing agent is hydrogen peroxide.

Advantageously, the chemical oxidizing agent(s) are present in a total content ranging from 0.001% to 50% by weight, preferably from 0.05% to 30% by weight, more preferentially from 0.1% to 20% by weight and even more preferentially from 1% to 15% by weight, relative to the total weight of the composition comprising them.

The second composition B included in the second compartment 3 of the device 1 of the invention also comprises one or more fatty alcohols and/or one or more nonionic surfactants.

Preferably, the second composition B comprises one or more chemical oxidizing agents, one or more fatty alcohols and one or more nonionic surfactants.

Fatty Alcohols

The term "fatty alcohol" means a long-chain aliphatic alcohol comprising from 8 to 40 carbon atoms and comprising at least one hydroxyl group OH. The fatty alcohols according to the invention are preferably non-oxyalkylenated and non-glycerolated.

The fatty alcohols according to the invention may be saturated or unsaturated, and linear or branched, and include from 8 to 40 carbon atoms.

The fatty alcohols according to the invention are neither (poly)oxyalkylenated nor (poly)glycerolated.

More preferentially, the fatty alcohols according to the invention are chosen from compounds having the structure R—OH with R denoting a linear or branched, saturated or unsaturated alkyl group optionally substituted with one or more hydroxyl groups, comprising from 8 to 40, better still from 10 to 30, or even from 12 to 24 and even better still from 14 to 22 carbon atoms.

The fatty alcohols may be chosen from solid fatty alcohols and liquid fatty alcohols, and mixtures thereof.

For the purposes of the present invention, the term "solid fatty alcohol" means a fatty alcohol with a melting point of greater than 25° C., preferably greater than or equal to 28° C., more preferentially greater than or equal to 30° C. at atmospheric pressure (1.013×10⁵ Pa).

The solid fatty alcohols may be chosen from saturated or unsaturated, linear or branched solid fatty alcohols, including from 8 to 40 carbon atoms.

The solid fatty alcohols that may be used according to the invention are preferably chosen from compounds having the structure R—OH with R denoting a saturated linear alkyl group, optionally substituted with one or more hydroxyl groups, comprising from 8 to 40, better still from 10 to 30, or even from 12 to 24 and even better still from 14 to 22 carbon atoms.

The solid fatty alcohols that may be used may be chosen, alone or as a mixture, from:
lauryl alcohol (or 1-dodecanol);
myristyl alcohol (or 1-tetradecanol);
cetyl alcohol (or 1-hexadecanol);
stearyl alcohol (or 1-octadecanol);
arachidyl alcohol (or 1-eicosanol);
behenyl alcohol (or 1-docosanol);
lignoceryl alcohol (or 1-tetracosanol);
ceryl alcohol (or 1-hexacosanol);
montanyl alcohol (or 1-octacosanol);
myricyl alcohol (or 1-triacontanol).

For the purposes of the present invention, the term "liquid fatty alcohol" means a fatty alcohol with a melting point of less than or equal to 25° C., preferably less than or equal to 20° C. at atmospheric pressure ($1.013 \times 10^5$ Pa).

The liquid fatty alcohols that may be used according to the invention are preferably chosen from compounds having the structure R—OH with R denoting a saturated or unsaturated, linear or branched, preferably unsaturated and/or branched, alkyl group optionally substituted with one or more hydroxyl groups, comprising from 8 to 40, better still from 10 to 30, or even from 12 to 24 and even better still from 14 to 22 carbon atoms.

The liquid fatty alcohols that may be used may be chosen, alone or as a mixture, from oleyl alcohol, linoleyl alcohol, linolenyl alcohol, isocetyl alcohol, isostearyl alcohol, 2-octyl-1-dodecanol, 2-butyloctanol, 2-hexyl-1-decanol, 2-decyl-1-tetradecanol and 2-tetradecyl-1-cetanol, and mixtures thereof.

Preferably, the fatty alcohol(s) are chosen from solid fatty alcohols, preferentially from saturated, preferably linear, $C_8$-$C_{40}$, notably $C_{10}$-$C_{32}$ or even $C_{12}$-$C_{24}$ fatty alcohols, more preferentially from cetyl alcohol, stearyl alcohol and mixtures thereof such as cetearyl alcohol.

The $C_8$ to $C_{40}$ fatty alcohol(s) may also be chosen from $C_8$ to $C_{40}$ liquid fatty alcohols; better still from unsaturated and/or branched $C_8$ to $C_{40}$ liquid fatty alcohols, preferentially from unsaturated and/or branched $C_{14}$ to $C_{22}$ alcohols, better still from oleyl alcohol, isostearyl alcohol, and mixtures thereof.

Preferably, the fatty alcohol(s) are chosen from cetyl alcohol, stearyl alcohol and mixtures thereof such as cetearyl alcohol.

Advantageously, when they are present, the fatty alcohols are present in a content ranging from 0.25% to 5% by weight, preferably from 0.5% to 3% by weight, more preferentially from 0.75% to 2.5% by weight, relative to the total weight of the composition comprising them.

Nonionic Suifactants

The nonionic surfactant(s) that may be used in the present invention are notably described, for example, in the *Handbook of Surfactants* by M. R. Porter, published by Blackie & Son (Glasgow and London), 1991, pages 116-178.

The nonionic surfactant(s) that may be used in the present invention are different from the fatty alcohols described previously.

Examples of nonionic surfactants that may be mentioned include the following compounds, alone or as a mixture:

oxyalkylenated ($C_8$-$C_{24}$)alkylphenols;

saturated or unsaturated, linear or branched, oxyalkylenated or glycerolated C8 to C40 alcohols, preferably including one or two fatty chains;

saturated or unsaturated, linear or branched, oxyalkylenated C8 to C30 fatty acid amides;

esters of saturated or unsaturated, linear or branched, C8 to C30 acids and of polyethylene glycols;

preferably oxyethylenated esters of saturated or unsaturated, linear or branched, C8 to C30 acids and of sorbitol;

fatty acid esters of sucrose;

C8-C30 fatty acid esters of sorbitan, oxyethylenated C8-C30 fatty acid esters of sorbitan, (C8-C30)alkyl(poly)glucosides and (C8-C30)alkenyl(poly)glucosides, which are optionally oxyalkylenated (0 to 10 oxyalkylene units) and comprise from 1 to 15 glucose units, (C8-C30)alkyl(poly) glucoside esters;

saturated or unsaturated oxyethylenated plant oils;

condensates of ethylene oxide and/or of propylene oxide;

N—(C8-C30)alkylglucamine and N—(C8-C30)acylmethylglucamine derivatives;

amine oxides.

They are notably chosen from alcohols, α-diols and (C1-C20)alkylphenols, these compounds being ethoxylated, propoxylated or glycerolated and bearing at least one fatty chain including, for example, from 8 to 24 carbon atoms and preferably from 8 to 18 carbon atoms, the number of ethylene oxide or propylene oxide groups possibly ranging notably from 1 to 200, and the number of glycerol groups possibly ranging notably from 1 to 30.

Mention may also be made of condensates of ethylene oxide and of propylene oxide with fatty alcohols; ethoxylated fatty amides preferably containing from 1 to 30 ethylene oxide units, polyglycerolated fatty amides including on average from 1 to 5, and in particular from 1.5 to 4, glycerol groups, ethoxylated fatty acid esters of sorbitan containing from 1 to 30 ethylene oxide units, fatty acid esters of sucrose, fatty acid esters of polyethylene glycol, (C6-C24 alkyl)polyglycosides, oxyethylenated plant oils, N—(C6-C24 alkyl)glucamine derivatives, amine oxides such as (C10-C14 alkyl)amine oxides or N—(C10-C14 acyl)aminopropylmorpholine oxides.

The C8-C30 and preferably C12-C22 fatty acid esters (notably monoesters, diesters and triesters) of sorbitan may be chosen from:

sorbitan caprylate; sorbitan cocoate; sorbitan isostearate; sorbitan laurate; sorbitan oleate; sorbitan palmitate; sorbitan stearate; sorbitan diisostearate; sorbitan dioleate; sorbitan distearate; sorbitan sesquicaprylate; sorbitan sesquiisostearate; sorbitan sesquioleate; sorbitan sesquistearate; sorbitan triisostearate; sorbitan trioleate; and sorbitan tristearate.

The polyoxyethylenated C8-C30 (preferably C12-C18) fatty acid esters (notably monoesters, diesters and triesters) of sorbitan notably containing from 2 to 20 mol of ethylene oxide may be chosen from polyoxyethylenated esters of C12-C18 fatty acids, in particular lauric, myristic, cetylic or stearic acid, of sorbitan notably containing from 2 to 30 mol of ethylene oxide, such as:

polyoxyethylenated sorbitan monolaurate (4 OE) (POLYSORBATE-21), polyoxyethylenated sorbitan monolaurate (20 OE) (POLYSORBATE-20), polyoxyethylenated sorbitan monopalmitate (20 OE) (POLYSORBATE-40), polyoxyethylenated sorbitan monostearate (20 OE) (POLYSORBATE-60), polyoxyethylenated sorbitan monostearate (4 OE) (POLYSORBATE-61), polyoxyethylenated sorbitan monooleate (20 OE) (POLYSORBATE-80), polyoxyethylenated sorbitan monooleate (5 OE) (POLYSORBATE-81), polyoxyethylenated sorbitan tristearate (20 OE) (POLYSORBATE-65), polyoxyethylenated sorbitan trioleate (20 OE) (POLYSORBATE-85).

The polyoxyethylenated C8-C30 (preferably C12-C18) fatty acid esters (notably monoesters, diesters, triesters and tetraesters) of sorbitan, notably containing from 2 to 20 mol of ethylene oxide, may be chosen from polyoxyethylenated esters, notably containing from 2 to 20 mol of ethylene oxide, such as of C12-C18 fatty acids, in particular lauric, myristic, cetylic or stearic acid, and of sorbitan, such as:

the ester polyoxyethylenated with 20 OE of sorbitan and of cocoic acid (PEG-20 sorbitan cocoate);

the polyoxyethylenated esters (notably containing from 2 to 20 OE) of sorbitan and of isostearic acid (such as PEG-2 sorbitan isostearate; PEG-5 sorbitan isostearate; PEG-20 sorbitan isostearate such as the product sold under the name Nikkol TI 10 V by the company Nikkol), the polyoxyethylenated esters (notably containing from 2 to 20 OE) of sorbitan and of lauric acid (such as PEG-10 sorbitan laurate), the polyoxyethylenated esters (notably containing from 2 to 20 OE) of sorbitan and of oleic acid containing 10 oxyethylene groups (such as PEG-6 sorbitan oleate; PEG-20 sorbitan oleate), the polyoxyethylenated esters (notably containing from 3 to 20 OE) of sorbitan and of stearic acid (such as PEG-3 sorbitan stearate; PEG-4 sorbitan stearate; PEG-6 sorbitan stearate).

The saturated or unsaturated, linear or branched, oxalkylenated C8 to C30 fatty acid amides are preferably chosen from saturated or unsaturated, linear or branched, oxyethylenated C8 to C30 fatty acid amides. Mention may notably be made of the compounds having the INCI name Trideceth-2 carboxamide MEA such as Amidet A15 sold by the company Kao, or the compounds having the INCI name PEG-4 rapeseedamide, notably sold under the name Amidet® N by the company Kao.

The nonionic surfactant(s) are preferably chosen from saturated or unsaturated, linear or branched, oxyalkylenated or glycerolated C8-C40 alcohols, saturated or unsaturated, linear or branched, oxyalkylenated C8 to C30 fatty acid amides, and also mixtures thereof.

More preferentially, the nonionic surfactants are chosen from saturated or unsaturated, linear or branched, oxyethylenated C8-C40 alcohols, saturated or unsaturated, linear or branched, oxyethylenated C8 to C30 fatty acid amides, and also mixtures thereof.

Advantageously, when they are present, the nonionic surfactant(s) are present in a total content ranging from 0.1% to 10% by weight, preferably from 0.2% to 5% by weight, more preferentially from 0.3% to 2% by weight and better still from 0.5% to 1.5% by weight, relative to the total weight of the composition comprising them. Advantageously, when they are present, the nonionic surfactant(s) are present in a total content of less than or equal to 1.5% by weight relative to the total weight of the composition comprising them.

Advantageously, when they are present, the nonionic surfactant(s) chosen from saturated or unsaturated, linear or branched, oxyalkylenated or glycerolated C8-C40 alcohols are present in a content ranging from 0.1% to 10% by weight, preferably from 0.2% to 5% by weight, more preferentially from 0.3% to 1.5% by weight, relative to the total weight of the composition. Advantageously, when they are present, the nonionic surfactant(s) chosen from saturated or unsaturated, linear or branched, oxyalkylenated or glycerolated C8-C40 alcohols are present in a content of less than or equal to 1.5% by weight relative to the total weight of the composition comprising them.

Advantageously, when they are present, the nonionic surfactant(s) chosen from saturated or unsaturated, linear or branched, oxyalkylenated C8 to C30 fatty acid amides are present in a content ranging from 0.1% to 10% by weight, preferably from 0.2% to 5% by weight, more preferentially from 0.5% to 1.5% by weight, relative to the total weight of the composition comprising them. Advantageously, when they are present, the nonionic surfactant(s) chosen from saturated or unsaturated, linear or branched, oxyalkylenated C8 to C30 fatty acid amides are present in a content of less than or equal to 1.5% by weight relative to the total weight of the composition comprising them.

Preferably, the second composition B included in the second compartment 3 contains one or more fatty alcohols, as defined above, and one or more nonionic surfactants chosen from saturated or unsaturated, linear or branched, oxyalkylenated or glycerolated C8-C40 alcohols, saturated or unsaturated, linear or branched, oxyalkylenated C8 to C30 fatty acid amides, and also mixtures thereof.

Preferably, the second composition B contains one or more fatty alcohols, as defined above, one or more nonionic surfactants chosen from saturated or unsaturated, linear or branched, oxyalkylenated or glycerolated C8-C40 alcohols, and one or more nonionic surfactants chosen from saturated or unsaturated, linear or branched, oxyalkylenated C8 to C30 fatty acid amides.

The Polyols

The second composition B included in the second compartment 3 of the device 1 of the invention may also optionally comprise one or more polyols.

For the purposes of the present invention, the term "polyol" means an organic compound constituted of a hydrocarbon-based chain optionally interrupted with one or more oxygen atoms and bearing at least two free hydroxyl groups (—OH) borne by different carbon atoms, this compound possibly being cyclic or acyclic, linear or branched, and saturated or unsaturated.

Preferably, the polyols are different from the fatty alcohols as defined above.

More particularly, the polyol(s) comprise from 2 to 30 hydroxyl groups, more preferentially from 2 to 10 hydroxyl groups, even more preferentially from 2 to 3 hydroxyl groups.

Preferably, the composition included in the second compartment of the device of the invention comprises one or more polyols.

More preferentially, the second composition B comprises one or more polyols chosen from diglycerol, glycerol, propylene glycol, propane-1,3-diol, 1,3-butylene glycol, pentane-1,2-diol, octane-1,2-diol, dipropylene glycol, hexylene glycol, ethylene glycol, polyethylene glycols, sorbitol, sugars, such as glucose, and mixtures thereof, preferably glycerol.

Advantageously, when they are present, the polyol(s) are present in a total content ranging from 0.1% to 2% by weight, preferably from 0.2% to 1.5% by weight, more preferentially from 0.3% to 1% by weight, relative to the total weight of the composition comprising them.

The first composition A comprising the oxidation dye(s) and the acrylic anionic associative polymer(s) and the second composition B comprising the chemical oxidizing agent (s), the fatty alcohol(s) and/or the nonionic surfactant(s), and optionally the polyol(s), are advantageously mixed in a ratio ranging from 1:2 to 2:1.

The compositions used in the device 1 according to the invention may also contain one or more additives such as anionic polymers different from the acrylic associative anionic polymers, cationic, nonionic, amphoteric or zwitterionic polymers, or mixtures thereof, anionic surfactants, cationic surfactants, amphoteric or zwitterionic surfactants, mineral or organic thickeners, sequestrants, penetrants, antioxidants, fragrances, dispersants or preserving agents.

The above additives may be present in an amount ranging from 0.01% to 20% by weight relative to the weight of each composition.

Process

A subject of the present invention is also a process for treating keratin fibres, in particular human keratin fibres such as the hair, using the device 1 of the invention.

The process of the invention may be a process for dyeing keratin fibres.

The process comprises a step of placing said compartments 2, 3 in communication so as to allow mixing of the compositions A and B as described previously in one of said compartments. The compositions may be mixed manually, for example by shaking the device, or by means of a mixing member, for example a bead, incorporated into the device.

The ready-to-use composition thus obtained may be applied to wet or dry keratin fibres, which may or may not have been rinsed, and also to any type of fair or dark, natural or dyed, permanent-waved, bleached or relaxed fibres.

The application to the fibres may be performed via any conventional means, in particular using a comb, a fine brush, a coarse brush, a sponge or with the fingers. The application may also be performed using an applicator 8 incorporated into the device of the invention as described previously.

The ready-to-use composition is applied to the keratin fibres in a leave-on time of between 1 minute and 1 hour, in particular between 2 minutes and 45 minutes, more particularly between 3 minutes and 30 minutes, better still between 3 and 20 minutes.

After said composition has been applied, the keratin fibres can optionally be rinsed.

The keratin fibres are then optionally dried or left to dry, for example at a temperature of greater than or equal to 30° C.

Advantageously, the process of the invention is a process for dyeing human keratin fibres such as the hair.

The invention also relates to the use of the device 1 of the invention for dyeing keratin fibres, in particular human keratin fibres such as the hair.

The examples that follow serve to illustrate the invention without, however, being limiting in nature.

EXAMPLES

In the examples that follow, all the amounts are given, unless otherwise indicated, as mass percentages of active material (AM) relative to the total weight of the composition.

Compositions A (for dyeing) and B (for oxidizing) are prepared from the ingredients whose contents are indicated in the tables below (AM: active material):

TABLE 1

| Composition A | |
| --- | --- |
| Fragrance | 0.75 |
| Ascorbic acid | 0.4 |
| Glycerol | 5 |
| EDTA | 0.15 |
| Thiolactic acid | 0.4 |
| 2,5-Toluenediamine | 1 |
| Acrylates/beheneth-25 methacrylate copolymer | 0.3 |
| Ethanolamine | 3.5 |
| m-Aminophenol | 0.5 |
| 2-Methylresorcinol | 0.51 |
| 4-Amino-2-hydroxytoluene | 0.024 |
| Sodium laureth sulfate | 2.1 |
| Sodium sulfite | 0.5 |

TABLE 1-continued

| Composition A | |
| --- | --- |
| Carbomer | 0.9 |
| Hydroxybenzomorpholine | 0.11 |
| 2-Methyl-5-hydroxyethylaminophenol | 0.024 |
| 2,4-Diaminophenoxyethanol HCl | 0.051 |
| Water | qs 100 |

TABLE 2

| Composition B | |
| --- | --- |
| Sodium salicylate | 0.035 |
| Glycerol | 0.5 |
| Tetrasodium etidronate | 0.06 |
| Phosphoric acid | qs pH 2.2 ± 0.2 |
| Hydrogen peroxide | 6 |
| Tetrasodium pyrophosphate | 0.04 |
| Cetearyl alcohol | 2.28 |
| Ceteareth-25 | 0.57 |
| Trideceth-2 carboxamide MEA | 0.85 |
| Water | qs 100 |

Compositions A and B are each packaged in one compartment of a device 1 comprising two compartments 2, 3. Said device is configured to allow said compartments 2, 3 to be placed in communication and thus to enable the mixing of compositions A and B in one of the compartments.

In details, the two compartments 2 and 3 are moved relative to each other on a vertical axis X-X' so as to release a passage between the two compartments 2, 3. Therefore, the two compartments 2, 3 are placed in fluid communication and composition B is mixed with composition A in compartment 2. Compositions A and B are mixed manually by shaking the device 1. After mixing, the ready-to-use composition obtained is applied to the keratin fibres via the dispensing orifice 7 of the device. The ready-to-use composition flows by gravity via the dispensing orifice 7.

The ratio of compositions A and B is 1:1.5.

The mixture leaves the device easily, with a good restitution, and spreads easily onto the head of hair. After a leave-on time of 5 minutes at room temperature, rinsing, washing with a standard shampoo and drying, the colouring obtained is powerful.

The invention claimed is:

1. A device comprising at least two compartments:
   i) a first compartment comprising a first composition comprising:
      one or more oxidation dyes, and
      one or more acrylic anionic associative polymers;
   ii) a second compartment comprising a second composition comprising:
      one or more chemical oxidizing agents,
      one or more fatty alcohols and/or one or more nonionic surfactants, and
      optionally one or more polyols,
   said device being configured to allow said first and second compartments to be placed in communication so as to enable the mixing of said compositions in one of said first and second compartments.

2. The device according to claim 1, characterized in that the oxidation dye(s) are chosen from oxidation bases and oxidation couplers.

3. The device according to claim 1, characterized in that the oxidation dye(s) are present in a total content ranging from 0.0001% to 10% by weight, relative to the total weight of the composition comprising them.

4. The device according to claim 1, characterized in that the acrylic anionic associative polymer(s) are chosen from copolymers including, among their monomers, an α,β-monoethyleniclly unsaturated carboxylic acid and an ester of an α,β-monoethylenically unsaturated carboxylic acid and of an oxyalkylenated fatty alcohol.

5. The device according to claim 1, characterized in that the acrylic anionic associative polymer(s) are present in a total content ranging from 0.01% to 5% by weight, relative to the total weight of the composition comprising them.

6. The device according to claim 1, characterized in that the chemical oxidizing agent(s) are chosen from hydrogen peroxide, urea peroxide, alkali metal bromates, persalts, potassium persulfate and ammonium persulfate, peracids and oxidase enzymes (with the optional cofactors thereof), and mixtures thereof.

7. The device according to claim 1, characterized in that the chemical oxidizing agent(s) are present in a content ranging from 0.001% to 50% by weight, relative to the total weight of the composition comprising them.

8. The device according to claim 1, characterized in that the fatty alcohol(s) are chosen from solid fatty alcohols.

9. The device according to claim 1, characterized in that the fatty alcohol(s) are present in a total content ranging from 0.25% to 5% by weight, relative to the total weight of the composition comprising them.

10. The device according to claim 1, characterized in that the nonionic surfactant(s) are chosen from saturated or unsaturated, linear or branched, oxyalkylenated or glycerolated C8-C40 alcohols, saturated or unsaturated, linear or branched, oxyalkylenated C8 to C30 fatty acid amides, and also mixtures thereof.

11. The device according to claim 1, characterized in that the nonionic surfactant(s) are present in a total content ranging from 0.1% to 10% by weight, relative to the total weight of the composition comprising them.

12. The device according to claim 1, characterized in that the polyol(s) are chosen from diglycerol, glycerol, propylene glycol, propane-1,3-diol, 1,3-butylene glycol, pentane-1,2-diol, octane-1,2-diol, dipropylene glycol, hexylene glycol, ethylene glycol, polyethylene glycols, sorbitol, sugars, and mixtures thereof.

13. The device according to claim 1, characterized in that the polyol(s) are present in a content ranging from 0.1% to 2% by weight relative to the total weight of the composition comprising them.

14. The device according to claim 1, characterized in that the at least two compartments can move relative to each other on a vertical axis so as to release a passage between said compartments allowing said compartments to be placed in communication, and the mixing of the first and second compositions.

15. The device according to claim 1, characterized in that the at least two compartments are separated by at least one temporary shut-off member.

16. The device according to claim 1, characterized in that the device comprises an applicator.

17. A process for treating keratin fibres using the device as described according to claim 1.

18. The device according to claim 15, characterized in that the temporary shut-off member comprises a cylindrical skirt surrounding said open end and a stopper connected to said cylindrical skirt.

19. The device according to claim 1, characterized in that it comprises at least one dispensing orifice for dispensing the ready-to-use composition obtained after mixing the first composition and the second composition.

* * * * *